US006822095B1

(12) United States Patent
Mais et al.

(10) Patent No.: US 6,822,095 B1
(45) Date of Patent: Nov. 23, 2004

(54) METHOD FOR PRODUCING 4,6-DICHLOROPYRIMIDINE

(75) Inventors: Franz-Josef Mais, Düsseldorf (DE); Günther Cramm, Leverkusen (DE); Alexander Klausener, Pulheim (DE); Guido Steffan, Odenthal (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/019,093

(22) PCT Filed: Jun. 13, 2000

(86) PCT No.: PCT/EP00/05416

§ 371 (c)(1),
(2), (4) Date: Dec. 19, 2001

(87) PCT Pub. No.: WO01/00591

PCT Pub. Date: Jan. 4, 2001

(30) Foreign Application Priority Data

Jun. 26, 1999 (DE) .......................................... 199 29 353

(51) Int. Cl.$^7$ ............................................ C07D 239/30
(52) U.S. Cl. ....................................................... 544/334
(58) Field of Search ................................ 544/344, 334

(56) References Cited

U.S. PATENT DOCUMENTS

| 5,723,612 A | 3/1998 | Huber et al. ................. 544/334 |
| 6,608,199 B2 * | 8/2003 | Doyle et al. ................. 544/319 |

FOREIGN PATENT DOCUMENTS

| DE | 44 08 404 | 9/1995 |
| DE | 195 31 299 | 2/1997 |
| DE | 196 42 533 | 4/1998 |
| EP | 0 095 637 | 12/1983 |
| EP | 95 637 | 12/1983 |
| EP | 697 406 | 2/1996 |
| EP | 745 593 | 12/1996 |
| GB | 2325224 A * | 11/1998 |
| GB | 2325224 | 11/1998 |
| WO | 95/29166 | 11/1995 |
| WO | WO 95/29166 A1 * | 11/1995 |
| WO | 96/23776 | 8/1996 |

OTHER PUBLICATIONS

Pauling, Linus, "General Chemistry, 2$^{nd}$ Ed.", 1953, W.H. Freeman, San Francisco, p. 86.*
Paquette, Leo A. Ed., "Encyclopedia of Reagents for Organic Synthesis, vol. 6", a995 John Wiley and Sons, New York, p. 1109.*

Dr Rod Beavon, "Rates sometimes fall" Oct. 17, 2003, [online]. London: Westminster School, [retrieved Mar. 17, 2004]. Retrieved from the Internet <http://www.rod.beavon.clara.net/nitrogenmonoxide.htm>.*

James A. Plambeck, "Termolecular Reactions Are Unlikely" Nov. 16, 1996, [online]. Edmonton, AL: University of Alberta, [retrieved on Mar. 17, 2004]. Retreived from the Internet <http://www.psigate.ac.uk/newsite/reference/plambeck/chem2/p02156.htm>.*

W. R. Salzman, "Reaction Mechanisms" Mar. 24, 2001, [online]. Tuscon, AZ: University of Arizona, [retrieved on Mar. 17, 2004]. Retreived from the Internet <http://www.chem.arizona.edu/~salzmanr/480a/480ants/reac-mech.html>.*

Fred Omega Garces, "Reaction Mechanism Steps of a Reaction" Oct. 16, 2000, [online]. San Diego, CA: Miramar College, [retrieved on Mar. 17, 2004]. Retreived from the Internet <http://www.miramar.sdccd.cc.ca.us/faculty/fgarces/zCourse/Fall2K/Ch201/Ch201Lec/Lectur>.*

Garner, James et al, Heterocyclic Communications, 5(6), 1999, pp. 503–508.*

John D. Roberts and Marjorie C. Caserio, "Basic Principles of Organic Chemistry", Benjamin, New York, 1964, p 257–259.*

Henry R. Henze, William J. Clegg, Charles W. Smart; J. Org. Chem.; 1952; 17(10); 1320–1327.*

Anonymous: "chlorination of pyrimidines" Research Disclosure Nr. 391, Nov. 1996, Seiten 690–691, XP000680903.

Takao Sakamoto et al.: "Condensed Heteroaromatic Ring Systems VII. Syntheisis of Thienopyridines, Thienopyrimidines, and Furopyridines from o–substituted N–Nheteroarylacetylenes", Chemical and Pharmaceutical Bulletin, Bd. 34, Nr. 7, 1986, Seiten 2719–2724, XP002066903.

Carroll Temple, Jr., et al.; "Preparation of 2,5–Diamino–4, 6–dichloropyrimidine", Journal of Organic Chemistry, Bd. 40, Nr. 21, 1975, Seiten 3141–3142, XP000566489.

James Garner et al.: "Regiocontrolled Amination of dichloropyrimidines in Liclo4–Et20 Solutions." Heterocyclic Communications, Bd. 5, Nr. 6, 1999, Seiten 503–508, XP000926047.

* cited by examiner

Primary Examiner—Thomas McKenzie
(74) Attorney, Agent, or Firm—Diderico van Eyl; Godfried R. Akorli

(57) ABSTRACT

The present invention relates to a process for preparing 4,6-dichloropyrimidine by reaction of 4-chloro-6-hydroxypyrimidine with an acid chloride.

9 Claims, No Drawings

METHOD FOR PRODUCING 4,6-DICHLOROPYRIMIDINE

The present invention relates to a process for preparing 4,6-dichloropyrimidine from 4-chloro-6-hydroxypyrimidine. 4,6-Dichloropyrimidine is a valuable intermediate for preparing crop protection agents.

A number of processes for preparing 4,6-dichloropyrimidine are known, see, for example, WO96/23776, EP-A-697 406, EP-A-745 593, WO 95/29166, DE-A-19 53 129 and GB 2 325 224. However, these processes always start from 4,6-dihydroxypyrimidine.

It is also known (see Res. Discl. n 391, 690–691 (1996)) that 4,6-dichloropyrimidine can be reacted by reacting 4-chloro-6-methoxypyrimidine with a chlorinating agent of the formula $R_3PCl_2$.

DE-A44 08 404 describes a process for preparing chloropyrimidines, including inter alia 4,6-dichloropyrimidine. Hydroxypyrimidines are generally mentioned as starting material, but not chlorohydroxypyrimidines. According to this reference, furthermore, chlorination is effected with $POCl_3$ with addition of amines or amine hydrochlorides.

No process for preparing 4,6-dichloropyrimidine starting from 4-chloro-6 hydroxypyrimidine and resulting in the desired product in a simple manner is yet known.

A process for preparing 4,6-dichloropyrimidine which is characterized in that 4-chloro-6-hydroxypyrimidine is reacted with an acid chloride has now been found.

Suitable acid chlorides are organic and inorganic acid chlorides, for example $PCl_3$, $POCl_3$, $PCl_5$, R—$PCl_2$, R—$PCl_4$, R—$POCl_2$ and $R_3PCl_2$, where R represents optionally substituted $C_6$–$C_{10}$-aryl or optionally substituted $C_1$–$C_{10}$-alkyl, acid chlorides of the formula R'—CO—Cl with R'=chlorine, $C_1$–$C_{10}$-alkoxy, $C_6$–$C_{10}$-aryloxy, —O—$CCl_3$, —CO—Cl, $C_5$–$C_{11}$-heteroaryloxy with 1 to 3 heteroatoms from the group of N, O and S, where the alkoxy, aryloxy and hetaryloxy radicals may optionally be substituted, and $SOCl_2$.

The acid chlorides are active on their own. In particular, no additions of catalysts are necessary, such as amides (for example diethylformamide), amines or organic phosphorus compounds (see EP-A-95 637).

However, it is possible to add such catalysts which are known in principle.

It is also possible to employ mixtures of acid chlorides, but this is not preferred.

It is furthermore possible to generate the required acid chloride in situ. For example, $R_3PCl_2$ can be generated from $R_3P$ and chlorine or from $R_3P$=O and a chlorinating agent, for example $PCl_3$, phosgene or $SOCl_2$.

It is furthermore possible to employ not only isolated 4-chloro-6-hydroxypyrimidine but also a reaction mixture which contains 4-chloro-6-hydroxypyrimidine and originates, for example, from the cleavage of 4-chloro-6-methoxypyridine. The acid chloride to be employed according to the invention can be metered directly into the reaction mixture from the cleavage of 4-chloro-6-methoxypyrimidine.

In general, at least 1 mol of acid chloride per mole of 4-chloro-6-hydroxypyrimidine is employed in the process of the invention. This amount is preferably 1 to 3 mol.

Solvents suitable in principle are those which have no adverse effect on the reaction to be carried out. Examples are aliphatic solvents such as alkanes, cycloalkanes and halogenoalkanes, aromatic solvents such as benzene, xylenes, toluene, chlorobenzenes, benzotrifluoride, p-chlorobenzotrifluoride and anisole, it being possible for the aliphatic and aromatic solvents optionally to be substituted further, nitriles such as acetonitrile and benzonitrile, N-containing solvents such as dimethylformamide, dimethylaceamide, lactams and cyclic ureas, and ethers and polyethers of a wide variety of types. A solvent can be dispensed with if liquid acid chlorides are employed, preferably in excess.

The process of the invention can be carried out, for example, at temperatures in the range 0 to 200° C., preferably at 20 to 175° C., particularly preferably at 30 to 150° C. The pressure is not critical. It can be, for example, 0.1 to 50 bar, preferably 0.5 to 5 bar. Atmospheric pressure is particularly preferred.

The process of the invention can be carried out in various embodiments, for example batchwise, semibatchwise or continuously. One possible procedure is as follows: 4-chloro-6-hydroxypyrimidine is added to an acid chloride with, where appropriate, a solvent. It is then possible to stir at the desired temperature until the conversion to the 4,6-dichloropyrimidine has taken place substantially or completely. It is also possible to meter the acid chloride into 4-chloro-6-hydroxypyrimidine in solution or as suspension. Other procedures are also conceivable.

The working up of the reaction mixture present after the reaction can take place, for example, by extraction of the prepared 4,6-dichloropyrimidine with a solvent and subsequent distillation of the extract. It is also possible to add water to the mixture present after the reaction and then remove 4,6-dichloropyrimidine. It is also possible to distil the complete reaction mixture or firstly carry out a rechlorination with $Cl_2/PCl_3$ or $PCl_5$ and then distil. Other embodiments and possible work ups are also conceivable.

The process of the invention for preparing 4,6-dichloropyrimidine is considerably simpler than the prior art processes. It requires no catalysts or auxiliaries such as amides, organic phosphorus compounds, amines or amine hydrochlorides. It can moreover be carried out without solvent if liquid acid chlorides are used, which greatly simplifies the working up.

EXAMPLES

Example 1

100 parts by weight of chlorobenzene, 13.1 parts by weight of 4-chloro-6-hydroxypyrimidine and 36.6 parts by weight of dichlorotriphenylphosphorane were introduced into a stirred vessel. The mixture was then heated with stirring to 100° C. and stirred at this temperature for 3 hours. After cooling to room temperature, the content of 4,6-dichloropyrimidine in the reaction mixture was found by HPLC to be 9.95% by weight. The yield taking account of the final weight of 144.3 parts by weight of reaction mixture was thus 96.7% of theory. Only traces of 4-chloro-6-hydroxypyrimidine were found in the reaction mixture.

Example 2

100 parts by weight of thionyl chloride, 30 parts by weight of triphenylphosphine oxide and 26.1 parts by weight of 4-chloro-6-hydroxypyrimidine were introduced into a stirred vessel and heated to reflux with stirring. After 6 hours, the reaction was stopped and, after cooling to room temperature, 130.1 parts by weight of reaction mixture were obtained and were analyzed by HPLC. The content of 4,6-dichloropyrimidine was found to be 22.04% by weight, corresponding to a yield of 99.2% of theory. 4-Chloro-6-hydroxypyrimidine was present only in traces in the reaction mixture after the reaction.

Example 3

130 parts by weight of phosphorus oxychloride and 26.1 parts by weight of 4-chloro-6-hydroxypyrimidine were introduced into a stirred vessel and heated to 100° C. with stirring. The reaction was complete after 30 minutes at 100° C. The final weight of reaction mixture after cooling to room temperature was 152.3 parts by weight.

Analysis thereof by HPLC showed a content of 19.25% 4,6-dichloropyrimidine, corresponding to a yield of 98.4% of theory.

The reaction mixture was worked up by extraction five times with 100 parts by weight of methylcyclohexane each time at 50 to 60° C. The combined extracts were evaporated in vacuo. A solid residue of 30.8 parts by weight remained. Its content of 4,6-dichloropyrimidine measured by HPLC was 95.8%, corresponding to a yield of 99.0% of theory.

Example 4

The procedure was as in Example 3 and resulted, after cooling, in a reaction mixture with a final weight of 152.8 parts by weight and with a 4,6-dichloropyrimidine content, analyzed by HPLC, of 19.18%, corresponding to a yield of 98.3% of theory.

The reaction mixture was worked up by adding 33.0 parts by weight of $PCl_3$, heating to 80° C. and, while stirring, passing in 14.2 parts by weight of chlorine gas over the course of one hour. The phosphorus oxychloride was then distilled out, initially under atmospheric pressure and then under gentle vacuum (200 mbar) at a bottom temperature of up to 65° C. Distillation was then carried out under 100 mbar. 4,6-Dichloropyrimidine was obtained in an amount of 27.8 parts by weight with a content of 99.0% (HPLC). This corresponds to a yield of 92.4% of theory.

Example 5

100 parts by weight of dichlorophenylphosphine oxide and 20.08 parts by weight of 4-chloro-6-hydroxypyrimidine were mixed and heated to 100° C. with stirring. This was stopped after 7 hours, and the mixture was cooled to room temperature. 116.0 parts by weight of reaction mixture which, according to HPLC analysis, had a content of 16.04% 4,6-dichloropyrimidine and of 3.05% 4-chloro-6-hydroxypyrimidine were obtained. This corresponds to a yield of 81.2% of 4,6-dichloropyrimidine and 17.6% of unreacted starting material.

Example 6

100 parts by weight of chlorobenzene, 26.1 parts by weight of 4-chloro-6-hydroxypyrimidine and 10 parts by weight of dimethylformamide were introduced into a stirred vessel. The mixture was heated to 100° C. with stirring and 99 parts by weight of phosgene were passed in at a constant rate over the course of 4 hours. Then, at 100° C., nitrogen was passed in for 1 hour to expel residues of phosgene. Cooling to room temperature resulted in 130.5 parts by weight of reaction mixture. HPLC analysis of the reaction mixture showed 19.8% 4,6-dichloropyrimidine, corresponding to a yield of 86.7% of theory.

Example 7

110 parts by weight of chlorobenzene, 26.1 parts by weight of 4-chloro-6-hydroxypyrimidine and 45.8 parts by weight of phosphorus pentachloride were introduced into a stirred vessel. The mixture was then heated to 100° C. with stirring. After one hour at 100° C., cooling to room temperature resulted in 175.9 parts by weight of reaction mixture. HPLC analysis thereof showed a content of 16.6% 4,6-dichloropyrimidine, which corresponds to a yield of 98.0% of theory.

Example 8

100 parts by weight of acetonitrile, 14.5 parts by weight of 4-chloro-6-methyoxypyrimidine and 0.03 parts by weight of water were introduced into a stirred vessel and, while stirring at 80° C., 37 parts by weight of hydrogen chloride gas were passed in over the course of 10 hours. An HPLC sample was then taken. This indicated that the 4-chloro-6-methyoxypyrimidine was almost completely reacted and 4-chloro-6-hydroxypyrimidine had resulted. The reaction mixture obtained in this way was stirred at 80° C. and, over the course of 1 hour, 30.7 parts by weight of phosphorus oxychloride were added at a constant rate. After stirring for 15 minutes, the mixture was concentrated in vacuo. This resulted in a brown residue which was extracted three times with 5 parts by weight of methylcyclohexane each time. Concentration of the combined methylcyclohexane extracts afforded a pale beige solid residue of 4,6-dichloropyrimidine. Final weight: 14.2 parts by weight, HPLC content 98.9%, corresponding to a yield of 94.3% of theory.

Example 9

The process of Example 8 was repeated. After the addition of 30.7 parts by weight and stirring for 15 minutes, 21 parts by weight of phosphorus pentachloride were added in portions. The mixture was then stirred for 30 minutes and completely distilled in a manner analogous to Example 4. 13.9 parts by weight of 4,6-dichloropyrimidine and an HPLC content of 99.1% were obtained. This corresponds to a yield of 92.4% of theory.

What is claimed is:

1. A process for preparing 4,6-dichloropyrimidine comprising reaching 4-chloro-6-hydroxypyrimidine with an acid chloride.

2. The process according to claim 1 wherein the acid chloride is $PCl_3$, $POCl_3$, $PCl_5$, R—$PCl_2$, R—$PCl_4$, R—$POCl_2$, or $R_3PCl_2$, where R represents $C_6$–$C_{10}$-aryl, substituted $C_6$–$C_{10}$-aryl, $C_1$–$C_{10}$-alkyl, or substituted $C_1$–$C_{10}$-alkyl; an acid chloride of the formula R'—CO—Cl, where R' represents chlorine, $C_1$–$C_{10}$-alkoxy, $C_6$–$C_{10}$-aryloxy, —O—$CCl_3$, —CO—Cl, or $C_5$–$C_{11}$-heteroaryloxy having 1 to 3 heteroatoms selected from the group consisting of N, O, and S, where the alkoxy, aryloxy, and heteroaryloxy radicals are optionally substituted; and $SOCl_2$.

3. The process according to claim 1 wherein the acid chloride is generated in situ.

4. The process according to claim 1 wherein 4-chloro-6-hydroxypyrimidine is used in isolated form or in the form of a reaction mixture containing the 4-chloro-6-hydroxypyrimidine and originating from the cleavage of 4-chloro-6-methoxy-pyrimidine.

5. The process according to claim 1 wherein at least 1 mol of acid chloride is used per mole of 4-chloro-6-hydroxypyrimidine.

6. The process according to claim 1 carried out in the presence of an aliphatic solvent, an aromatic solvent, a nitrile, an N-containing solvent, an ether, or a polyether.

7. The process according to claim 1 carried out at a temperature in the range 0 to 200° C.

8. The process according to claim 1 carried out under a pressure in the range 0.1 to 50 bar.

9. The process according to claim 1 wherein 4-chloro-6-hydroxypyrimidine is added to the acid chloride, optionally with a solvent.

* * * * *